US009442081B2

(12) United States Patent
Odén et al.

(10) Patent No.: US 9,442,081 B2
(45) Date of Patent: Sep. 13, 2016

(54) METHOD AND APPARATUS FOR ESTIMATING THE ASH CONTENT OF A BIOLOGICAL MATERIAL

(75) Inventors: Erik Odén, Taby (SE); Ragnar Kullenberg, Oskarstrom (SE); Anders Ullberg, Aby (SE); Fredrik Danielsson, Ekero (SE)

(73) Assignee: MANTEX AB, Kista (SE)

( * ) Notice: Subject to any disclaimer, the term of this patent is extended or adjusted under 35 U.S.C. 154(b) by 423 days.

(21) Appl. No.: 13/575,071

(22) PCT Filed: Jan. 26, 2011

(86) PCT No.: PCT/EP2011/051047
§ 371 (c)(1),
(2), (4) Date: Aug. 20, 2012

(87) PCT Pub. No.: WO2011/092192
PCT Pub. Date: Aug. 4, 2011

(65) Prior Publication Data
US 2013/0195243 A1    Aug. 1, 2013

(30) Foreign Application Priority Data

Jan. 28, 2010   (EP) .................................... 10151990

(51) Int. Cl.
*G01N 23/087*   (2006.01)
*G01N 23/06*    (2006.01)

(52) U.S. Cl.
CPC .............. *G01N 23/087* (2013.01); *G01N 23/06* (2013.01); *G01N 2223/612* (2013.01)

(58) Field of Classification Search
CPC ........ A61B 6/482; A61B 6/505; G01N 23/06; G01N 23/087; G01N 23/16; G01N 2223/612; G01N 2223/613; G01N 2223/617; G01N 2223/619
USPC ........... 378/41, 51, 53, 54, 56, 57, 58, 62, 83, 378/88, 156
See application file for complete search history.

(56) References Cited

U.S. PATENT DOCUMENTS 3,452,193 A * 6/1969 Petersen ......................... 378/53
5,014,288 A * 5/1991 Chase et al. .................... 378/53
(Continued)

FOREIGN PATENT DOCUMENTS

DE    265696        3/1989
WO    0109596       2/2001
WO    2011092192    8/2011

OTHER PUBLICATIONS

International Search Report for PCT/EP2011/051047, Completed by the European Patent Office on Mar. 29, 2011, 2 Pages.
Norberg., Vattenfall Research and Development AB Aug. 22, 2007, 74 Pages, "On-Line Quality Control of Solid Fuels Detection and Separation Techniques.".
Nordel., Varmeforsk Service AB Apr. 2000, ISSN: 0282-3772, English translation attached or original, All together 78 Pages, "Measurements of Mositure Contect in Wood Fuels With Dual Energy X-ray."
(Continued)

*Primary Examiner* — Glen Kao
*Assistant Examiner* — Julio M Duarte-Carvajalino
(74) *Attorney, Agent, or Firm* — Brooks Kushman P.C.

(57) ABSTRACT

A method for measuring ash content in a biological material in an automated or semi-automated procedure is disclosed. The method includes the steps of scanning the biological material with electromagnetic radiation of at least two different energy levels, determining the amount of radiation transmitted through the sample of the biological material at the energy levels and estimating the moisture content in the biological material based on a relationship between the determined amount of radiation transmitted through the biological material. Thereafter, the ash content in the biological material is estimated, based on the estimated moisture content in the biological material, and average attenuation coefficients for the biological material without moisture, attenuation coefficients for a combustible part of the biological material and attenuation coefficients for ash of the biological material at the energy levels. A corresponding apparatus is also disclosed.

17 Claims, 2 Drawing Sheets

(56) References Cited

U.S. PATENT DOCUMENTS

| | | | | |
|---|---|---|---|---|
| 5,809,104 | A | * | 9/1998 | Kullenberg et al. ............ 378/54 |
| 6,151,379 | A | * | 11/2000 | Kullenberg et al. ............ 378/54 |
| 8,467,496 | B2 | * | 6/2013 | Ullberg et al. .................. 378/53 |
| 2009/0310744 | A1 | * | 12/2009 | Petch et al. ..................... 378/53 |
| 2010/0219109 | A1 | * | 9/2010 | Roos et al. ..................... 209/3.1 |

OTHER PUBLICATIONS

Mitchell et al. Poult. Sci. Dec. 1997, vol. 76, No. 12, p. 1746-1752, "Body Composition Analysis of Chickens by Dual Energy X-Ray Absorptiometry."

* cited by examiner

METHOD AND APPARATUS FOR ESTIMATING THE ASH CONTENT OF A BIOLOGICAL MATERIAL

CROSS-REFERENCE TO RELATED APPLICATION

This application is the U.S. national phase of PCT Appln. No. PCT/EP2011/051047 filed on 26 Jan. 2011, which claims priority to EP Patent Application No. 10151990.8 filed on 28 Jan. 2010, the disclosures of which are incorporated in their entirety by reference herein.

TECHNICAL FIELD OF THE INVENTION

The present invention relates to a method and an apparatus for measuring the ash content of a biological material in an automated or semi-automated procedure. The invention is particularly useful for measuring the ash content in biofuels, such as wood chips and coal.

BACKGROUND

Biomass fuels are commonly used in burn processes for generation of heat and energy. One of the most important biomass fuels is wood. However, different biomass fuels generate different amount of heat and different amount and type of residuals after burning. Great deviations exist also for different types and qualities of wood. This makes it difficult to control a burning or combustion process effectively.

The effective thermal value of a specific biomass fuel can be determined relatively precisely if the moisture content and ash content for the biomass fuel is known. However, heretofore, fast and accurate estimation of both moisture content and ash content have been difficult to achieve in practice.

Ash from biomass, such as wood, typically comes from the minerals present in the structure of e.g. trees and shrubs in addition to any soil contamination and other contaminations. Properties of wood ash depend on a variety of factors including the type of tree or shrub, the part of the tree or shrub (bark, wood, leaves), type of waste (wood, pulp, or paper residue), type of soil and climate and conditions of combustion.

Agricultural residues typically generate significantly more ash than woody biomass. Typically, the ash content in wood is about 0.5 percent, whereas it is 5 to 10 percent in diverse agricultural crop materials, and up to 30 to 40 percent in rice husks and milfoil.

The composition and amount of ash affects the biomass behavior under the high temperatures of combustion and gasification. For example, melted ash may cause problems in both combustion and gasification reactors. These problems can e.g. be clogged ash removal systems caused by slagging ash, fouling of burners and boilers from ash deposition, and severe operating problems in fluidized bed systems. When wood is combusted alone, ash deposition is not typically a problem because combustion temperatures are likely to be low. However, when biomass is co-fired with coal, combustion temperatures are considerably higher and may reach a level where slagging could occur.

There is therefore a need for a fast and accurate method and system for determining ash content of a biological material, and in particular for biomass fuels, which can e.g. be used directly by people in field work operation, be used in automated processes, and the like.

SUMMARY OF THE INVENTION

It is therefore an object of the present invention to provide an improved method and apparatus for estimating the ash content in a biological material in an automated or semi-automated process, which overcome or at least alleviate the above-discussed problems of the prior art.

This object is achieved by means of the invention as defined in the appended claims.

According to a first aspect of the invention there is provided a method for estimating ash contents in a biological material, comprising the steps of:

scan the biological material with electromagnetic radiation of at least two different energy levels; determine the amount of radiation transmitted through said sample of the biological material at said energy levels;

estimate the moisture content in the biological material based on a relationship between said determined amount of radiation transmitted through the biological material at said energy levels; and estimating the ash content in said biological material, based on said estimated moisture content in the biological material, and average attenuation coefficients for the biological material without moisture, attenuation coefficients for a combustible part of the biological material and attenuation coefficients for the ash of the biological material at said energy levels.

The present invention is particularly useable for estimating the ash content in biomass fuels, but it is also useable for other biological materials. In particular, it is useable for estimating the ash content of wood chips, but it may also be used for other forms of wood, as well as for other types of biological material, such as pulp, biomass fuel, coal, etc. It may also be used for processed biomass, such as lignite, torrefied biomass and hydrothermal carbon (HTC). The invention is particularly useful for biological materials in a liquid or separated form, and preferably in the form of chips.

Ash content is in the present application used to denominate the residual remaining after ashing, and preferably the residual remaining after burning/combustion at 575±25° C. The ash content may be expressed in percent of dry material, i.e.

$$\text{ash content} = \frac{\text{(weight of sample after ashing)}}{\text{(weight of dried sample before ashing)}} * 100$$

By "moisture content" is in this application meant the ratio between the quantity of moisture (i.e. water) in a certain quantity of material and the total material quantity. Consequently, estimation of moisture content in a material is also, indirectly, an estimation of the non-moisture content. In e.g. wood chips, the material essentially consists of moisture on the one hand and fibers and ash content on the other.

The ash of biomass fuels typically comprises materials such as silicon, magnesium, aluminum, iron and calcium. The ash content has a great influence on the thermal value of the biomass. An increased ash content corresponds to a decreased thermal value. Thus, by estimation of the ash content it is also possible to deduce the thermal value of the biomass, and thus its usefulness. It is also possible to control the burning/combustion process in relation to the ash contents, in order to obtain a more effective burning/combustion, and avoid ash related problems, such as slagging and the like.

The combustible part of the biological material, i.e. the part which does not constitute moisture or ash content, typically predominantly comprises carbohydrates and lignin. For wood, the carbohydrate concentration is typically in the range 65-75%. Lignin concentration is typically in the range 18-35%.

It is to be acknowledged by the skilled addressee that the estimate of moisture content in the biological material, and calculation of the average attenuation coefficients for the biological material without moisture at said energy levels need not be distinguishable steps or made explicitly. It is also possible to integrate these steps in an integrated equation or calculation routine, arriving directly at the estimation of the ash content in the biological material.

The method of the present invention makes use of irradiation of two or more different energy levels, and determines the ash content of the material, directly or indirectly, from the measured transmission energy, i.e. the amount of the radiation of each wavelength that is absorbed in the material.

The step of determining the attenuation coefficient for moisture at the at least two energy levels is preferably made by means of reference measurements. Similarly, the step of determining the attenuation coefficients for the combustible part of the biological material and the ash of the biological material at the two or more energy levels is also preferably made by means of reference measurements.

Irradiation of the material is preferably made by scanning of the biological material with electromagnetic radiation of at least two different energy levels, wherein the biological material is arranged in a separated form, and preferably in the form of chips.

The method/apparatus according to the present invention is very well suited for use in online measurements along conveyor lines where material is transported, in pipe-lines, on conveyor belts etc. This is possible, since e.g. the present invention can be used for various and varying heights and forms of the biological material.

However, the present invention is also very useable for measuring samples of material arranged in sample containers, e.g. for sample testing in process industries, in the field measurements, etc.

Thus, the present invention may be used in fully or partly automated procedures, and requires no, or very limited, operator interaction.

The determined ash content can be used as input for the control of subsequent processing of the biological material. Hereby, the subsequent use of the biological material becomes more efficient. For example, this information could be used for obtaining more efficient purification, incineration, combustion, etc. Further, the ash content may be used to generate an alarm or the like e.g. when a predetermined threshold value is exceeded. The sending of this information to the control system and the use of said information for the control of the subsequent process may also be automated. When used in an in-line system, the subsequent process can hereby be controlled in real-time based on said information. However, it is also possible to store the information for later use in association with the specific sample or batch of biological material.

Thus, in one line of embodiments, the scanning of the biological material with electromagnetic radiation of at least two different energy levels comprises arranging the biological material in a sample container.

In another line of embodiments, the scanning of the biological material with electromagnetic radiation of at least two different energy levels comprises scanning the biological material as it is continuously conveyed through a point of measure.

The amount of radiation transmitted through the sample of the biological material at the two energy levels is preferably determined in relation to a calibration reference value. The calibration reference value can e.g. be determined by measurement of the transmission of radiation through a reference material of a predetermined thickness, which is preferably made immediately before and/or after the each measurement through the biological material, the reference material e.g. being aluminum. Hereby, it is ensured that adequate calibration is always at hand.

Further, the moisture content of the sample of biological material is preferably based on a determination of a K-value for the biological material, said K-value being calculated as:

$$K = \frac{\ln(N_{01}/N_1)}{\ln(N_{02}/N_2)}$$

wherein $N_{01}$, $N_{02}$ are the calibrated reference values for the transmission at the two energy levels and $N_1$, $N_2$ are the transmission values through the biological material at said energy levels, and estimation of the moisture content of said biological material by comparing said calculated K-value with corresponding K-values for a similar material type, e.g. provided in the form of a reference database. It has been found by the present inventors that the K-value is relatively linear for many types of biological material, in particular for many sorts of wood, and accordingly, relatively few specific values in the reference database for each type of biological material can still be used to provide accurate estimations of a broad range of moisture content values in the sample material. The ash content for each sample may be regarded as more or less constant. When the K-values are linearly dependent on the moisture content, it may even be sufficient to store only two different K-values in the reference database.

The scanning of the sample of the biological material with electromagnetic radiation of at least two different energy levels may comprises a first scan with a first energy level, and a subsequent second scan with a second energy level.

The at least two different energy levels are both preferably of X-ray radiation wavelengths. Further, the radiation of both said energy levels are preferably emitted from a single radiation source operating in the energy range 20-150 kVp. Here, kVp (Peak kilovoltage) denotes the maximum voltage applied across an X-ray tube. It determines the kinetic energy of the electrons accelerated in the X-ray tube and the peak energy of the X-ray emission spectrum. The actual voltage across the tube may fluctuate.

According to another aspect of the invention, there is provided an apparatus for estimating ash contents in a biological material in comprising:

a scanning device for scanning a sample of the biological material with electromagnetic radiation of at least two different energy levels;

a detector for determining the amount of radiation transmitted through said sample of the biological material at said energy levels; and a processor for estimating the moisture content in the biological material based on said determined amounts of radiation transmitted through the sample, and estimating the ash content in said biological material, based on said estimated moisture content in the biological material, and average attenuation coefficients for the biological material without moisture, attenuation coefficients for the combustible part of the biological material and attenuation coefficients of the ash content of the biological material at said energy levels.

This aspect of the invention provides similar advantages as discussed above in relation to the first aspect.

The irradiation of two or more different energy levels is preferably achieved by means of two or more radiation sources, such as two or more X-ray tubes. Preferably, the irradiation at each energy level derives from a separate radiation source.

Alternatively or additionally, the irradiation of two or more different energy levels is preferably detected by means of two or more detectors. Preferably, the irradiation at each energy level is detected in a separate radiation detector.

These and other aspects of the invention will be apparent from and elicidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DETAILED DESCRIPTION OF PREFERRED EMBODIMENTS

Figure 1:
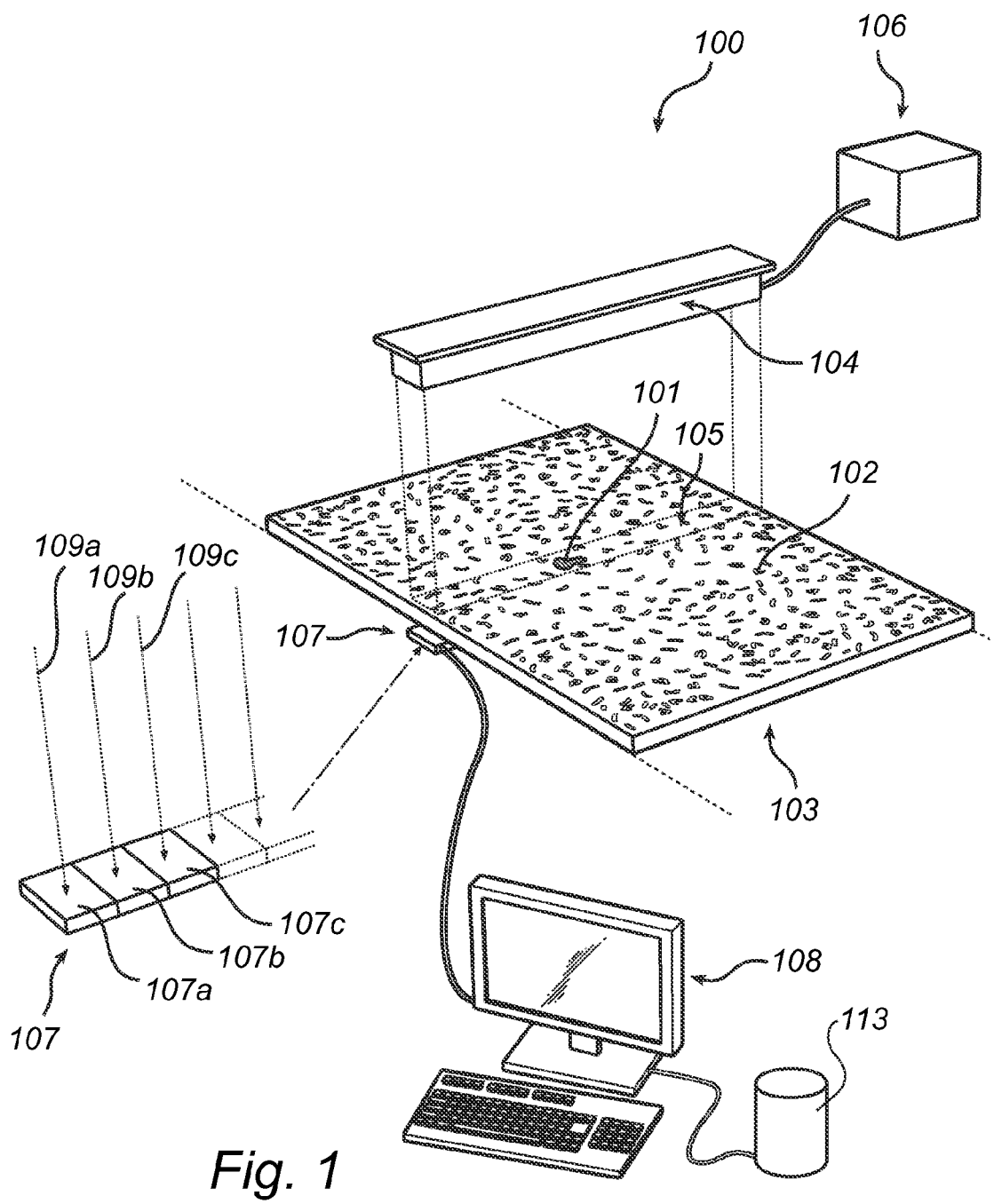
FIG. 1 schematically illustrates a measurement device for detecting ash content in a biological material transported on a conveyor line.

FIG. 1 schematically illustrates an embodiment of a measurement device 100 for estimating ash content present in a biological material 102 transported on a conveyor line 103. The biological material 102 may typically be wood chips, or other biomass fuels.

In order to scan all of the material moved past the measurement device, the measurement device comprises a radiation source 104 adapted to irradiate a target area 105 that spans across the width of the conveyor line. The radiation source 104 is adapted to provide radiation of at least two different energy levels/wavelengths. Preferably, the radiation source is an X-ray tube for provision of X-ray radiation of two or more different wavelengths. Preferably, the X-ray tube operates in the range 20-150 kVp. The output radiation from the radiation source is preferably directed towards the target area through a collimator and a lens (not shown). The radiation source 104 is controlled by means of a controller 106.

Alternatively, the radiation source 104 may comprise two or several separate juxtaposed radiation tubes, wherein the juxtaposed radiation sources radiate the different wavelengths either simultaneously or sequentially. However, preferably the different wavelength radiation traverses the material to be measured along essentially the same path. When radiation of two (or more) wavelengths is emitted simultaneously from the radiation source the intensity of the two signals should preferably be measured individually. This may be effected directly by making provisions such that certain portions of the detector by filtration only measure radiation having a certain energy level while others measure other energy levels. It may also be effected by subsequent treatment of signals, allowing superimposed signals to be separated.

On the opposite side of the target area 105, a detector 107 is arranged to receive radiation transmitted through material located in the target area 105. The detector is preferably a semiconductor detector comprising a linear array of semiconductor detector areas 107a-c distributed across the width of the conveyor line. The number of detector areas may vary due to the expected variations of ash content in the material, etc. The detector 107 is connected to a control unit 108 with a processor, e.g. an ordinary personal computer. The control unit receives detection data from the detector through a suitable interface, such as through a USB port.

In operation, the radiation source 104 irradiates the material in the target area 105 with electromagnetic radiation of at least two different energy levels. This may be achieved by sequentially irradiating the material with radiation of a first wavelength, and radiation of a second wavelength, i.e. the radiation source initially emits rays having one wavelength and then, by altering the voltage across the radiation tube, a different wavelength.

For each energy level, the amount of radiation transmitted through the material located in the target area 105 is measured on the opposite side of the target area 105 by the detector areas 107a-c of the detector, wherein each detector area 107a-c receives radiation that has penetrated the material 102 along a different radiation path 109a-c.

In order to get a reference value for calibration, it is preferred to measure a reference material. This can be achieved, for example, by measuring without any biological material present. Thus, in this case, a reference measurement is obtained with air as a reference material. Alternatively, the biological material may be replaced with a reference material with known properties, such as aluminum. The reference measurements may be obtained before measuring of the biological material, during initialization, or repeatedly during the process. Alternatively, reference measurements may be obtained by relocating the radiation source 104 and the detector 107 to a location next to the conveyor line such that the radiation passes through air only on its way from the radiation source to the detector. It is also possible to use additional radiation sources and detectors situated on one or both sides of the conveyor belt.

Based on these reference measurements, calibration reference values are determined as:

$$N_{01,02} = N_{Air1,2} \exp(\mu x)$$

where $N_{01}$ and $N_{02}$ are the calibration reference values for energy level 1 and 2, respectively, $N_{Air1}$ and $N_{Air2}$ are the detected transmission values after passage through the known distance of air, $\mu$ is the known attenuation coefficient for air ($cm^{-1}$) and x is the known distance of air (cm) that separates the radiation source and the detector.

A K-value for the material is determined for the radiation received by each detector area 107a-c. The K-value is calculated as:

$$K = \frac{\ln(N_{01}/N_1)}{\ln(N_{02}/N_2)}$$

wherein $N_{01}$, $N_{02}$ are the calibrated reference values for the transmission at the two energy levels and $N_1$, $N_2$ are the transmission values through the biological material at the energy levels.

Based on these measurement data, the moisture content in the biological material is then estimated. Estimation of the moisture content of the biological material can e.g. be estimated by comparing the calculated K-value with corresponding K-values for a similar material type available from a reference database.

The reference database 113 can preferably be connected to the control unit 108, with data concerning at least detected transmission values for the radiation at the different energy levels, and moisture content values, for different types of biological material, such as for a number of different sorts of wood. The selection of a suitable type of biological material in the reference database may be provided by means of manual input.

However, it is also possible to determine the type of biological material automatically. Such automated determination of material type can e.g. be obtained in the way described in PCT-application with application number EP2009/062767 by the same applicant, said document hereby incorporated by reference.

The data for the reference database is preferably assembled by measuring transmission of electromagnetic radiation of at least two different energy levels through a plurality of different material types, and by measuring the moisture content of said materials by means of a conventional method, and preferably by controlled drying. The material types may e.g. be different sorts of wood, such as birch, spruce, pine, oak, and alder, and also coal and other biofuels. Hereby, the same type of measurement data as obtained with the subsequent measurement of new materials can be related to exactly measured moisture content data. Since the reference database need only be created during the initialization, and can then be reused repeatedly, there is no particular need for speedy processes during these reference database measurements.

The matching of the K-value to K-values in the reference database may either be based on identification of the closest K-value identifiable in the reference database for the specific type of material at hand, and using the corresponding moisture value as the estimate for the sample. A correction may also be used in order to compensate for the difference between the actual K-value and the identified closest K-value in the reference database.

Alternatively, the K-values for the specific material type may be used in a linear or polynomial representation of the correspondence between the K-value and the moisture content, and this function may then be used for an estimate of the moisture content corresponding to the K-value of the sample material.

Thereafter, the average attenuation coefficients for the biological material without moisture at said energy levels are calculated. The total attenuation through the material at each energy level comprises three parts: attenuation in the moisture content (water) and the attenuation in the non-moisture content, i.e. dry combustible material and ash. The attenuation in the moisture content depends on the attenuation coefficient for moisture at the specific energy level. The attenuation in the non-moisture content similarly depends on the average attenuation coefficient for the non-moisture content at the specific energy level, i.e. on the average coefficient for the dry combustible material and the average attenuation coefficient for the ash. By means of the estimation of the moisture content discussed above, the amount of moisture and non-moisture in the material are now known. Further, the attenuation coefficient for moisture (water) at the specific energy level is easily determinable, e.g. from reference literature or from specific reference measurements.

Since all other parameters are known, the average attenuation coefficients for the biological material without moisture at said energy levels can then be estimated, based on the amount of radiation transmitted through the sample of the biological material at the two energy levels and the attenuation coefficients for moisture at these energy levels.

The average attenuation coefficients for the dry biological material are hereby estimated, and may then finally be used to estimate the ash content in the biological material. The attenuation in the non-moisture content at each energy level also comprises two parts: attenuation in the ash content of the biological material, and the attenuation in the combustible part of the biological material.

The attenuation coefficients for the combustible part of the biological material and the ash of the biological material, respectively, at the two energy levels are determinable, e.g. from reference literature or from specific measurements, since the type of biological material is known, and expected constituents of the ash may also be known, or determined by specific reference measurements.

Accordingly, at this point there are consequently two equations available, one for each energy level, with a total of two unknowns—the amount of combustible biological material and the amount of ash content, respectively. By solving this set of equations, an estimate is obtained for the amount of combustible dry biological material on the one hand, and for the amount of ash content on the other.

Thus, as a final step, the ash content of the biological material is estimated, based on the average attenuation coefficients for the biological material without moisture and attenuation coefficients for a combustible part of the biological material and ash of the biological material at the two energy levels. The determined ash content of the biological material may be used as an indirect measure of the amount of energy that can be obtained from the biological material. It may also be used to issue an alarm signal or the like if the ash content exceeds a certain threshold value or the like.

All the calculations are preferably made in the control unit 108.

Figure 2A:
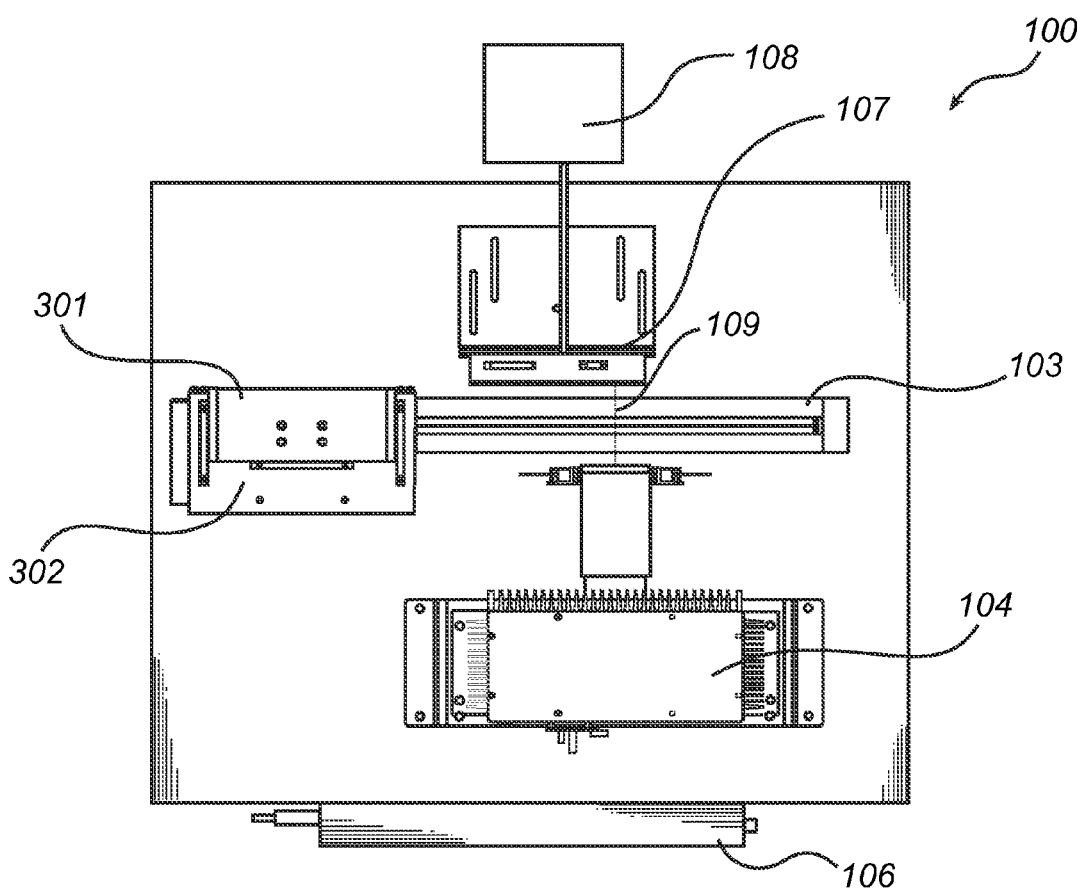
FIG. 2a-b schematically illustrates an embodiment of the invention where the material to be measured is arranged in a sample container.
Figure 2B:
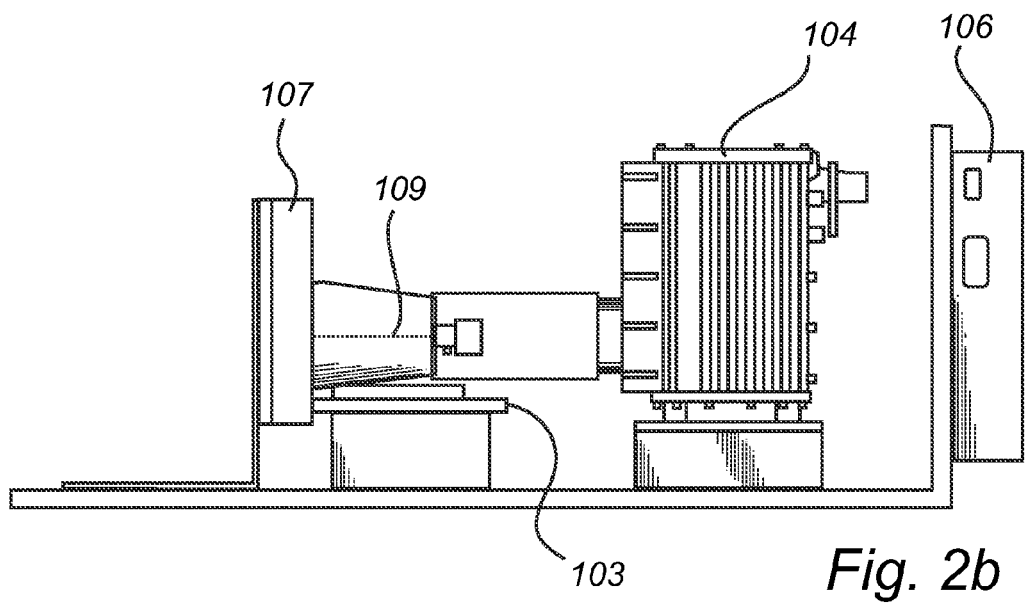

FIG. 2*a-b* schematically illustrates an alternative embodiment of a measurement device according the invention. The measurement device 100 comprises a radiation source 104 for irradiating a target area with at least two energy levels. The radiation source is controlled by means of a controller 106. A detector 107 is arranged on the opposite side of the target area. The detector is connected to a control unit 108 that receives detection data from the detector. In this embodiment, the material to be measured is arranged in a sample container 301. The sample container is then arranged on a carrier 302, which is movable in such a way that the sample container is moved through the target area, and thus through the radiation path 109. The carrier may e.g. be moved by means of a conveyor 103. However, other means for moving the carrier are also feasible, such as linear motors, screw arrangements, rail arrangements and the like.

During operation, the sample container is moved through the target area such that preferably all of the material in the sample container is scanned. At the first passage, the material sample is irradiated with radiation of a first wavelength, and in the second passage, during the return movement, with radiation of a second wavelength. In order to get a reference value for calibration, it is preferred to measure a reference material, preferably a predetermined amount of aluminum, at the beginning and end of the passage of the sample container.

Based on these reference measurements, calibration reference values are determined as:

$$N_{O1,O2} = N_{Al1,2} \exp(\mu x)$$

where $N_{O1}$ and $N_{O2}$ are the calibration reference values for energy level 1 and 2, respectively, $N_{Al1}$ and $N_{Al2}$ are the detected transmission values after passage through the known thickness of aluminum, $\mu$ is the known attenuation coefficient for aluminum (cm$^{-1}$) and x is the known thickness of the aluminum (cm).

Thereafter, a K-value for the biological material may be calculated as:

$$K = \frac{\ln(N_{01}/N_1)}{\ln(N_{02}/N_2)}$$

wherein $N_{01}$, $N_{02}$ are the calibrated reference values for the transmission at the two energy levels and $N_1$, $N_2$ are the transmission values through the biological material at the energy levels.

The ash content of the biological material may then be determined in the same way as has been previously been described for the embodiment illustrated in FIG. 1.

According to another embodiment, the ash content is directly estimated based on the measured radiation energy transmitted through the material at the two energy levels and the estimated moisture content, estimated in accordance with the method discussed above.

Based on these input values, the following equation system with three equations can be formulated:

$$N_1 = N_{01}\exp(\mu_{v1}X + \mu_{t1}Y + \mu_{a1}Z)$$

$$N_2 = N_{02}\exp(\mu_{v2}X + \mu_{t2}Y + \mu_{a2}Z)$$

$$F = X/(X+Y+Z)$$

where $\mu_{v1}$, $\mu_{t1}$ and $\mu_{a1}$ are mass attenuation coefficients for the first energy level for water, dry combustible biomaterial and ash. Similarly, $\mu_{v2}$, $\mu_{t2}$ and $\mu_{a2}$ are mass attenuation coefficients for the second energy level for water, dry combustible biomaterial and ash.

X, Y and Z are area masses (g/cm$^2$) for water, dry combustible biomass and ash. The resulting value F is the moisture content defined as ((weight of non-dry bio material–weight of dry bio material)/weight of non-dry bio material).

All the mass attenuation coefficients for water, ash and dry combustible bio material are known (see above). These can e.g. be determined by separate reference measurements in the system. The moisture content can be determined based on the K-value as discussed above.

Accordingly, it is possible to formulate a direct equation for Z (the ash content) for the bio material in accordance with the following:

$$Z = \frac{(F-1)\mu_{t_2}R_1 + \mu_{t_1}R_2 - F(\mu_{v_2}R_1 + \mu_{t_1}R_2 - \mu_{v_1}R_2)}{\mu_{a_2}((F-1)\mu_{t_1} - F\mu_{v_1}) + \mu_{a_1}(\mu_{t_2} - F\mu_{t_2} + F\mu_{v_2}) + F(\mu_{t_2}\mu_{v_1} - \mu_{t_1}\mu_{v_2})}$$

where $R_1$ is $\ln(N_{01}/N_1)$ and $R_2$ is $\ln(N_{02}/N_2)$.

Specific embodiments of the invention have now been described. However, several alternatives are possible, as would be apparent for someone skilled in the art. For example, the radiation need not be X-ray, but other types of electromagnetic radiation may also be used. Further, other relations between the two measured amounts of radiation transmitted through the sample of the biological material at the two energy levels may be used, instead of the K-value discussed above. Still further, it would also be possible to use three or more energy levels, in order to obtain an even higher degree of accuracy. Further, there are various ways of determining the type of biological material, both automatically and semi-automatically. Depending on the intended line of use, the reference database can be customized to comprise only the most probable material types, or comprise a large variety of different material types. Still further, the implementation of the control and processing method could be accomplished in different ways, such as in especially dedicated hardware or in software for control of already existing control means.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A method for estimating ash contents in a biological material, comprising steps of:
scanning the biological material with X-ray radiation of at least two different energy levels;
determining an amount of X-ray radiation transmitted through a sample of the biological material at the at least two different energy levels;
estimating a moisture content in the biological material based on a relationship between the determined amount of X-ray radiation transmitted through the biological material at the energy levels; and
estimating the ash content in the biological material, based on the estimated moisture content in the biological material, average attenuation coefficients for the biological material without moisture, attenuation coefficients for a combustible part of the biological material, and attenuation coefficients for ash of the biological material at the energy levels;
wherein the moisture content of the sample of the biological material is determined by determination of a K-value for the biological material, the K-value being calculated as:

$$K = \frac{\ln(N_{01}/N_1)}{\ln(N_{02}/N_2)}$$

wherein N01, N02 are calibrated reference values for transmission at the at least two different energy levels and N1, N2 are transmission values through the biological material at the energy levels, and the estimating of the moisture content of the biological material is done by comparing the calculated K-value with corresponding K-values for a similar material type.

2. The method of claim 1, further comprising a step of determining the attenuation coefficient for moisture at the energy levels by reference measurements.

3. The method of claim 1, further comprising a step of determining the attenuation coefficients for a combustible part of the biological material and the ash of the biological material at the energy levels by reference measurements.

4. The method of claim 1, wherein the scanning of the biological material with X-ray radiation of the at least two different energy levels comprises arranging the biological material in a separated form.

5. The method of claim 4, wherein the separated form is in the form of chips.

6. The method of claim 5, wherein the method comprises at least one X-ray radiation source for each specific energy level.

7. The method of claim 6, wherein there is provided at least one detector for each specific energy level.

8. The method of claim 1, wherein the scanning of the biological material with X-ray radiation of the at least two different energy levels comprises arranging the biological material in a sample container.

9. The method of claim 1, wherein the scanning of the biological material with X-ray radiation of the at least two different energy levels comprises scanning the biological material as it is continuously conveyed through a point of measure.

10. The method of claim 1, wherein the amount of X-ray radiation transmitted through the sample of the biological material at the at least two different energy levels is determined in relation to a calibration reference value.

11. The method of claim 10, wherein the calibration reference value is determined by measurement of the transmission of X-ray radiation through a reference material of a predetermined thickness, the calibration measurement being made immediately before and/or after each measurement through the biological material.

12. The method of claim 1, wherein the scanning of the sample of the biological material with X-ray radiation of the at least two different energy levels comprises a first scan with a first energy level, and a subsequent second scan with a second energy level.

13. The method of claim 1, wherein the at least two different energy levels both are of X-ray radiation wavelengths.

14. The method of claim 1, wherein the X-ray radiation of both the energy levels are emitted from a single X-ray radiation source operating in an energy range of about 20-150 kVp.

15. The method of claim 1, wherein a reference material is aluminum.

16. An apparatus for estimating ash contents in a biological material comprising:
- a scanning device for scanning a sample of the biological material with X-ray radiation of at least two different energy levels;
- a detector for determining an amount of X-ray radiation transmitted through the sample of the biological material at the at least two different energy levels; and
- a processor programed to estimate the moisture content in the biological material based on determined amounts of radiation transmitted through the sample, estimate ash content in the biological material, based on the estimated moisture content and average attenuation coefficients for the biological material without moisture, attenuation coefficients for a combustible part of the biological material, and attenuation coefficients for the ash content of the biological material at the energy levels, wherein the moisture content of the sample of the biological material is determined by determination of a K-value for the biological material, the K-value being calculated as:

$$K = \frac{\ln(N_{01}/N_1)}{\ln(N_{02}/N_2)}$$

wherein N01, N02 are calibrated reference values for transmission at the at least two different energy levels and N1, N2 are transmission values through the biological material at the energy levels, and the estimating of the moisture content of the biological material is done by comparing the calculated K-value with corresponding K-values for a similar material type.

17. The apparatus of claim 16, wherein there are provided at least two detectors for determining the amount of X-ray radiation transmitted through the sample of the biological material at the energy levels.

* * * * *